(12) United States Patent
Schnetz et al.

(10) Patent No.: US 10,058,478 B2
(45) Date of Patent: Aug. 28, 2018

(54) ELECTRICAL STIMULATION DEVICE

(71) Applicant: BIEGLER GMBH, Mauerbach (AT)

(72) Inventors: Guntram Schnetz, Biedermannsdorf (AT); Friedrich Netauschek, Hoeflein an der Donau (AT)

(73) Assignee: Biegler GmbH, Mauerbach (AT)

( * ) Notice: Subject to any disclaimer, the term of this patent is extended or adjusted under 35 U.S.C. 154(b) by 145 days.

(21) Appl. No.: 14/652,619

(22) PCT Filed: Dec. 12, 2013

(86) PCT No.: PCT/AT2013/050250
§ 371 (c)(1),
(2) Date: Jun. 16, 2015

(87) PCT Pub. No.: WO2014/094021
PCT Pub. Date: Jun. 26, 2014

(65) Prior Publication Data
US 2015/0335885 A1    Nov. 26, 2015

(30) Foreign Application Priority Data
Dec. 20, 2012   (AT) .................................. 50127/2012

(51) Int. Cl.
*A61N 1/00* (2006.01)
*A61H 39/00* (2006.01)
(Continued)

(52) U.S. Cl.
CPC ......... *A61H 39/002* (2013.01); *A61N 1/0502* (2013.01); *A61N 1/36017* (2013.01); *A61H 2201/165* (2013.01); *A61H 2205/027* (2013.01)

(58) Field of Classification Search
CPC .............. A61N 1/0502; A61N 1/36017; A61N 1/37247
(Continued)

(56) References Cited

U.S. PATENT DOCUMENTS

| 6,564,102 B1 | 5/2003 | Boveja |
| 2008/0288016 A1 | 11/2008 | Amurthur |
| (Continued) | | |

FOREIGN PATENT DOCUMENTS

| AT | 395106 B | 9/1992 |
| EP | 2168630 A1 | 3/2010 |
| WO | 2012000003 A1 | 1/2012 |

OTHER PUBLICATIONS

International Preliminary Report on Patentability [PCT/AT2013/050250] dated Jul. 2, 2015.

*Primary Examiner* — Amanda Hulbert
*Assistant Examiner* — Philip C Edwards
(74) *Attorney, Agent, or Firm* — Edwin S. Flores; Daniel J. Chalker; Chalker Flores, LLP

(57) ABSTRACT

The invention relates to an electrical stimulation device (1) having a stimulator (2), containing a generator (3) for generating electrical stimulation pulses having specific stimulation parameters, a voltage supply (4) for supplying the generator (3) with electrical energy and a stimulator housing (13), and having at least two needle electrodes (5) for piercing the surface of the skin of an area to be stimulated, which needle electrodes (5) are connected to the stimulator (2) via a line (7), wherein the stimulator (2) can be releasably connected to a fastening element (14) for fastening the stimulator (2) to the surface of the skin. In order to fasten the stimulator (2) to the surface of the skin of a patient in an easier and better manner, the fastening element (14) has a clip (15) for releasably receiving the stimulator housing (13) and a support element (16) for supporting and fastening the stimulator (2) to the surface of the skin.

14 Claims, 5 Drawing Sheets

(51) Int. Cl.
*A61N 1/05* (2006.01)
*A61N 1/36* (2006.01)

(58) Field of Classification Search
USPC .......................................................... 607/46
See application file for complete search history.

(56) References Cited

U.S. PATENT DOCUMENTS

| | | | | |
|---|---|---|---|---|
| 2009/0157146 | A1* | 6/2009 | Linder | A61N 1/37217 607/60 |
| 2009/0182393 | A1* | 7/2009 | Bachinski | A61N 1/37264 607/59 |
| 2010/0042180 | A1* | 2/2010 | Mueller | A61N 1/0456 607/46 |
| 2010/0274327 | A1* | 10/2010 | Carroll | A61N 1/0456 607/72 |

* cited by examiner

ELECTRICAL STIMULATION DEVICE

The invention relates to an electrical stimulation device having a stimulator, containing a generator for generating electrical stimulation pulses having specific stimulation parameters, a voltage supply for supplying the generator with electrical energy and a stimulator housing, and having at least two needle electrodes for piercing the surface of the skin of an area to be stimulated, which needle electrodes are connected to the stimulator via a line, wherein the stimulator can be releasably connected to a fastening element for fastening the stimulator to the surface of the skin.

The relevant electrical stimulation device may be used for electro-acupuncture therapy, mainly on persons, but also on animals. In particular, the device is suited for the use of electrical stimulation in the region of the ears. Application areas range from pain therapy and the healing of wounds to the therapy of a disturbed blood flow, for example in diabetics.

An electrical stimulation device of the present type is known from WO 2012/000003 A1, for example. Therein, the electrode housing containing the needle electrodes is attached to the surface of the skin of the area to be stimulated by means of adhesive foil and connected to the stimulator via a line. The stimulator may also be affixed to the surface of the skin near the area to be stimulated by means of an adhesive, or it may be disposed around the neck or the shoulder by means of a neck strap.

Especially in case of longer treatment times in the range of a few days, attaching the stimulator by an adhesive is a problem because the attachment has to be renewed after taking a shower.

The object of the present invention is to provide an electrical stimulation device as mentioned above, in which the drawbacks mentioned may be avoided or at least reduced, and which allows an easier fastening of the stimulator to the surface of the skin near the area to be stimulated.

The object according to the invention is achieved by an electrical stimulation device as mentioned above, wherein the fastening element has a clip for releasably receiving the stimulator housing and a support element for supporting and fastening the stimulator to the surface of the skin. The releasable connection of the stimulator by means of a fastening element may allow a separation of the actual stimulating function of the stimulator from the fastening function. Since the stimulator may be releasably connected to the fastening element, multiple fastening elements may be provided within one set, so the stimulator of the stimulation device may also be fastened to the surface of the skin multiple times during the duration of the treatment. Compared to the stimulator, the fastening element may be produced much more economically. Provided the fastening element is constructed appropriately, a swift, simple and secure fastening to the surface of the skin at a desired location may be accomplished. The clip of the fastening element spans the stimulator housing and receives it during operation of the electrical stimulation device. Preferably, the connection of the stimulator housing to the clip of the fastening element may be performed without using tools or additional aids. The support element of the fastening element serves to support and fasten the stimulator to the surface of the skin. Depending on the embodiment and the desired location for fastening the stimulator, fastening may be accomplished by means of double-sided adhesive tape, adhesive foil or an elastic tape having a quick fastener, in particular a velcro fastener.

In particular when the fastening is accomplished by an adhesive, it is advantageous if the clip of the fastening element is oriented at substantially 90° to the support element. This angular arrangement of the clip with respect to the support element of the fastening element prevents the clip from adversely affecting the fastening of the support element to the surface of the skin when connecting and releasing the stimulator.

According to a further feature of the invention the clip of the fastening element has latching elements for snapping into at least one groove in the stimulator housing. Such an implementation of the releasable connection between the stimulator housing and the fastening element may be made in a simple and economical manner and does not require additional aids for making and releasing the connection between the stimulator housing and the fastening element. Of course, the clip may also have a groove, and corresponding latching elements for snapping into this groove in the clip may be provided on the stimulator housing.

Here, it is advantageous if the at least one groove is disposed asymmetrically on the stimulator housing so the stimulator housing may only be connected to the fastening element in one orientation. In this way, placing the stimulator incorrectly on the clip may be avoided.

Advantageously, the at least two needle electrodes are disposed in a common electrode housing. In this way, production is simplified, but a defined distance between the at least two needle electrodes is obtained as well, which may be crucial for electrical stimulation. In addition, piercing the surface of the skin by the needle electrodes is substantially simplified when compared to single needle electrodes. During electro-acupuncture in the region of the ears of a person, in particular, the needle electrodes have a diameter of only some tenths of a millimeter and a piercing depth of a few millimeters, so handling single needle electrodes would be virtually impossible.

For attaching the electrode housing to the surface of the skin, preferably an appropriately shaped adhesive foil is provided. This adhesive foil may be provided independently from the electrode housing or may already be included therein. By pulling off a protective sheet as usual, the adhesive layer is exposed and may then be affixed to the desired location on the surface of the skin. In order to avoid skin irritations, the adhesives must be made of a suitable bio-compatible material. A certain permeability of the adhesive foil to air and moisture may be an advantage and improve acceptance.

Advantageously, an adhesive foil for attaching the fastening element to the surface of the skin is provided as well. This adhesive foil is also shaped appropriately or already present on the fastening element. In this way, the stimulator is also attached to the surface of the skin.

Advantageously, the adhesive foil has a much larger contact area than the fastening element and projects over it. Due to this, a larger adhesive area and, consequently, a secure hold of the stimulator on the surface of the skin may be obtained.

In order to be able to obtain a separation of the needle electrodes from the stimulator and remove the stimulator, for example when taking a shower, it is advantageous if the line is provided with at least one plug for releasably connecting it to a corresponding jack in the stimulator or the electrode housing. In this way, the patient or a caregiver can separate or reconnect the electrode housing from or to the stimulator easily. The line may be fixedly connected to the electrode housing, with the plug being attached at the end of the line and the stimulator being provided with a corresponding jack.

Similarly, it is possible to connect the line fixedly to the stimulator and to dispose the plug at the end of the line and the corresponding jack in the electrode housing.

Preferably, the plug is designed waterproof in order to allow taking a shower with the needle electrodes attached even when the stimulator is connected and fastened.

If a notch is disposed between the at least two needle electrodes on the side of the electrode housing facing the surface of the skin, a short circuit between the needle electrodes due to the production of sweat may be prevented effectively and, thus, a malfunction of the stimulation device may be avoided or at least its probability be reduced.

In order to be able to give feedback on the function of the stimulator to the patient or physician, an operation indicator is preferably disposed on the stimulator. Depending on the size of the stimulator, this operation indicator may be formed by one or more light-emitting diodes but also by displays. In addition to a visual operation indicator, an audible indication of proper operation and/or proper start-up may also be used.

If a control element is disposed on the stimulator, the stimulation parameters may be changed, for example.

This control element may be formed by a Hall sensor that may be actuated by a magnet. This prevents the patient from unintentionally or intentionally making changes to the stimulation parameters or deactivating the stimulator. A waterproof design of the stimulator is also facilitated by such an implementation of the control element. The attending physician, however, may make changes by means of such a contact-free control. Corresponding feedback may be output by visual or audible signals.

Advantageously, the stimulator includes a timer for automatically specifying the duration and possibly the pattern of the stimulation. After the desired duration of the treatment and the desired pattern of treatment have ended, the device switches off by itself.

The present invention is discussed in more detail with reference to the attached drawings. In the drawings.

Figure 1:
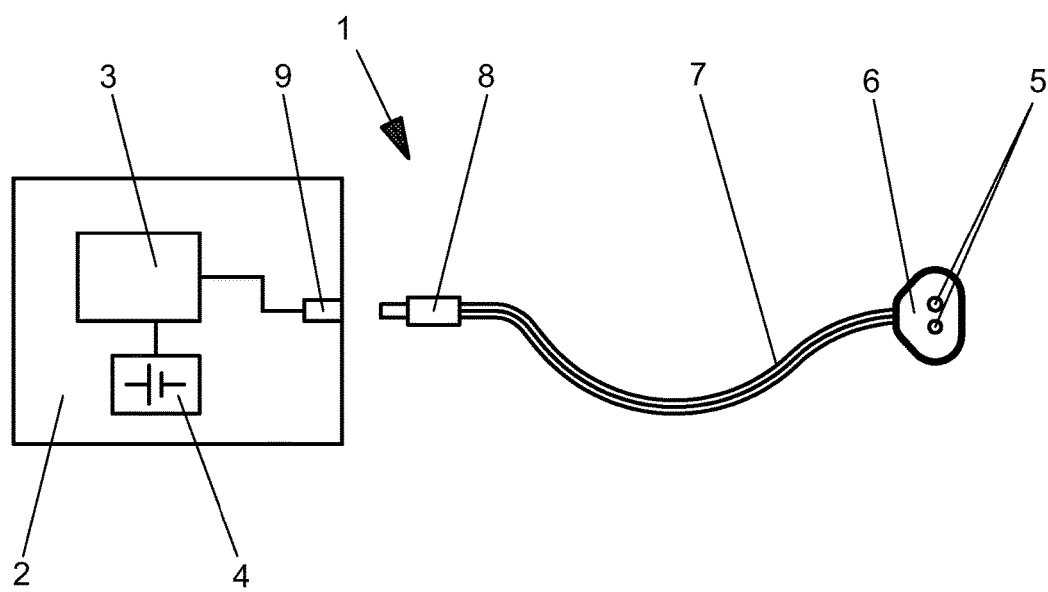
FIG. 1 shows a schematic block diagram of an embodiment of an electrical stimulation device.

FIG. 1 shows an electrical stimulation device 1, in particular for stimulation in the region of the ears of a person. The electrical stimulation device 1 includes a stimulator 2, containing a generator 3 for generating electrical stimulation pulses having specific stimulation parameters, i. e. certain voltage or certain current, certain duration, certain repetition rate and duty cycle, etc. For supplying the components of the stimulator 2 with electrical energy, a voltage supply 4 is provided, which is preferably formed by a suitable battery or rechargeable battery. The electrical pulses generated in the generator 3 of the stimulator 2 are output via at least two needle electrodes 5, which are pierced into the surface of the skin in the area to be stimulated. At least one ground electrode and at least one stimulation electrode are disposed in a common electrode housing 6. The needle electrodes 5 are connected to the stimulator 2 via a suitable line 7. By disposing all needle electrodes 5 together in the common electrode housing 6, easy application is made possible, and a better hold of the needle electrodes 5, in particular during longer intervals of therapy, and a defined distance between the individual needle electrodes 5 is obtained. The line 7 for connecting the needle electrodes 5 to the stimulator 2 may be disposed fixedly, i. e. inseparably, or releasably. For easy separation and connection it is advantageous if at least one corresponding plug 8 is disposed on the line 7. Depending on whether the line 7 is connected fixedly to the electrode housing 6 or the stimulator 2, the jack 9 associated to the plug 8 is located in the stimulator 2 or in the electrode housing 6 (not illustrated). If the line 7 is designed as a helix cable, length compensation between the electrode housing 6 and the stimulator 2 and better mobility may be obtained.

Figure 2:
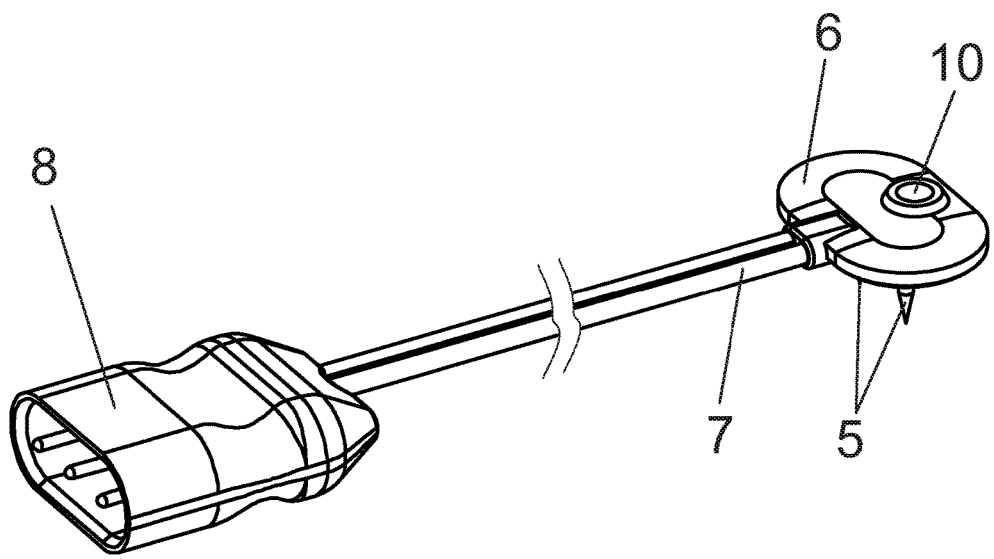
FIG. 2 shows an embodiment of an electrode housing having two needle electrodes and a line for connecting it to the stimulator.
Figure 3:
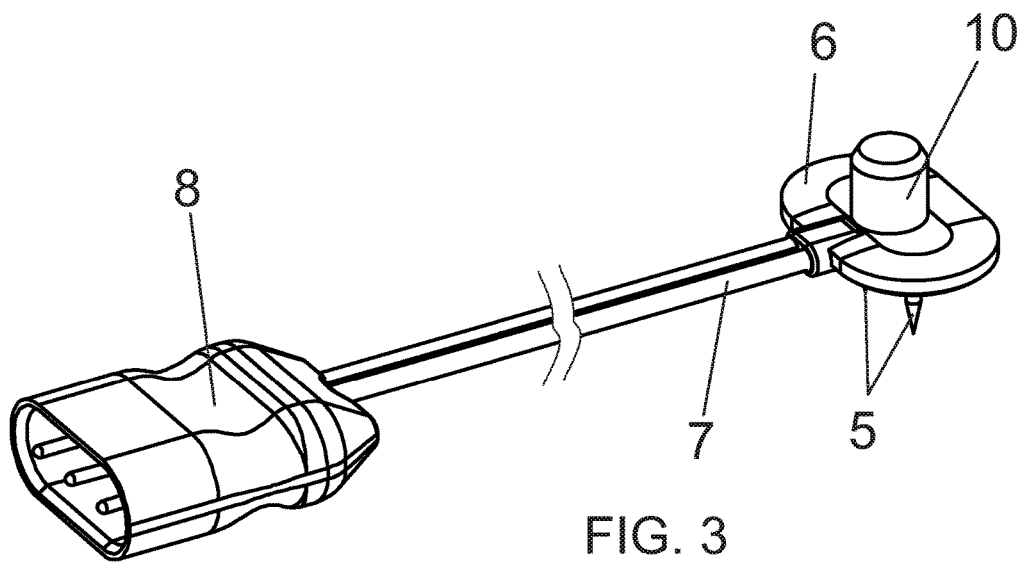
FIG. 3 shows a further embodiment of an electrode housing having two needle electrodes and a line for connecting it to the stimulator.

FIGS. 2 and 3 show two embodiments of an electrode housing 6 having needle electrodes 5 disposed therein and a fixedly connected line 7 having a plug 8 disposed thereon. The electrode housing 6, which is preferably made of plastic and preferably designed in a waterproof manner, may have a handling element 10 on the side opposite the needle electrodes 5 for facilitating the applying of the needle electrodes 5 to the desired area of the skin to be stimulated. For example, the handling element may be formed by a recess (FIG. 2) or a substantially cylindrical handle (FIG. 3). In the exemplary embodiment illustrated, the plug 8 has three contacts even though only two needle electrodes 5 are provided. This arrangement, which is discussed in more detail with reference to FIG. 7, makes it possible to automatically activate the electrical stimulation device 1 when plugging the needle electrodes 5 into the stimulator 2.

Figure 4:
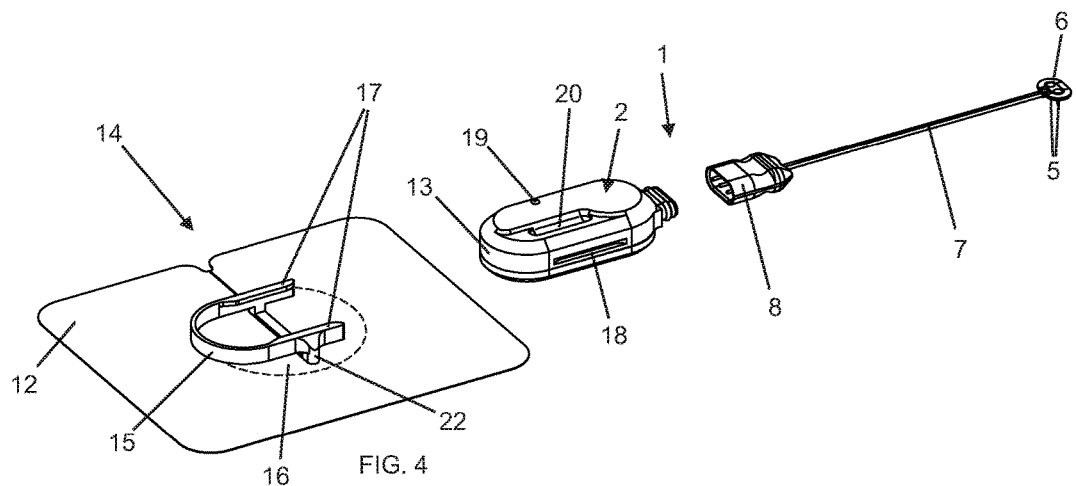
FIG. 4 shows an embodiment of a clip fastening of the stimulator in separated state.
Figure 5:
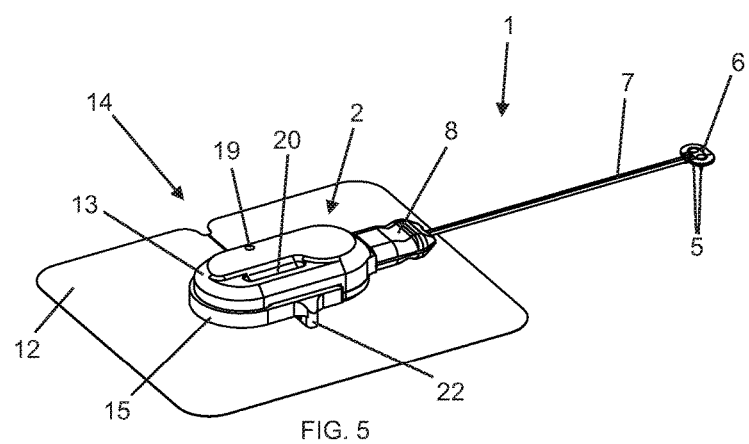
FIG. 5 shows the embodiment of the clip fastening of the stimulator according to FIG. 4 in connected state.

Referring to FIGS. 4 and 5, an embodiment of a releasable fastening of the stimulator 2 to a fastening element 14 according to the invention is discussed. In the illustration according to FIG. 4, the stimulator 2 of the electrical stimulation device 1 is illustrated separated from the needle electrodes 5 and from the fastening element 14, whereas the electrical stimulation device 1 according to FIG. 5 is illustrated in assembled state, i. e. with the needle electrodes 5 connected and the fastening element 14 connected. According to the invention, the stimulator 2 may be releasably connected to the fastening element 14. For this, the fastening element 14 has a clip 15 for releasably receiving the stimulator housing 13 of the stimulator 2 and a support element 16 (illustrated by a dashed line) connected to the clip 15 for supporting and fastening the stimulator 2 to the surface of the skin. The clip 15 and the support element 16 of the fastening element 14 may be manufactured very economically from plastic, for example in an injection-moulding process. The fastening to the surface of the skin may be accomplished directly via the support element 16 by providing the bottom side of the support element 16 with an adhesive layer. Alternatively, attaching the support element 16 may also be performed by an appropriately shaped adhesive foil 12. The adhesive foil 12 has a protective sheet (not illustrated) that may be pulled off at the bottom side, which is pulled off before application in order to expose the adhesive layer, as is common with a plaster. The clip 15 of the fastening element 14 is preferably disposed at substantially 90° to the support element 16 in order to prevent pulling the support element 16 from the surface of the skin when separating the stimulator 2 from the fastening element 14. The clip 15 has latching elements 17 for snapping into at least one groove 18 in the stimulator housing 13. The groove 18 is disposed asymmetrically in the stimulator housing 13 in order to allow pushing the stimulator 2 into the clip 15 in only one orientation. This guarantees access to a possible operation indicator 19 and a possible control element 20 on the stimulator 2. The control element 20 may be designed in a contact-free manner by disposing a Hall sensor which may be actuated by a magnet (see FIG. 6) in the stimulator 2. For facilitating the separation of the stimulator 2 from the fastening element 14, a lever 22 for spreading the arms of the clip 15 and lifting the latch elements 17 out of the groove 18 may be disposed on the clip 15.

A correspondingly designed electrical stimulation element 1 may also be shipped and distributed having multiple fastening elements 14 in order to allow multiple fastening of the stimulator 2 to the surface of the skin of the patient, for example during the duration of a treatment over several days. Since the fastening element 14 together with the adhesive foil 12 may be produced relatively economically and is separated from the stimulator 2, several of said fastening elements 14 may be added to a set without having to considerably raise the purchase price of the electrical stimulation device 1.

Figure 6:
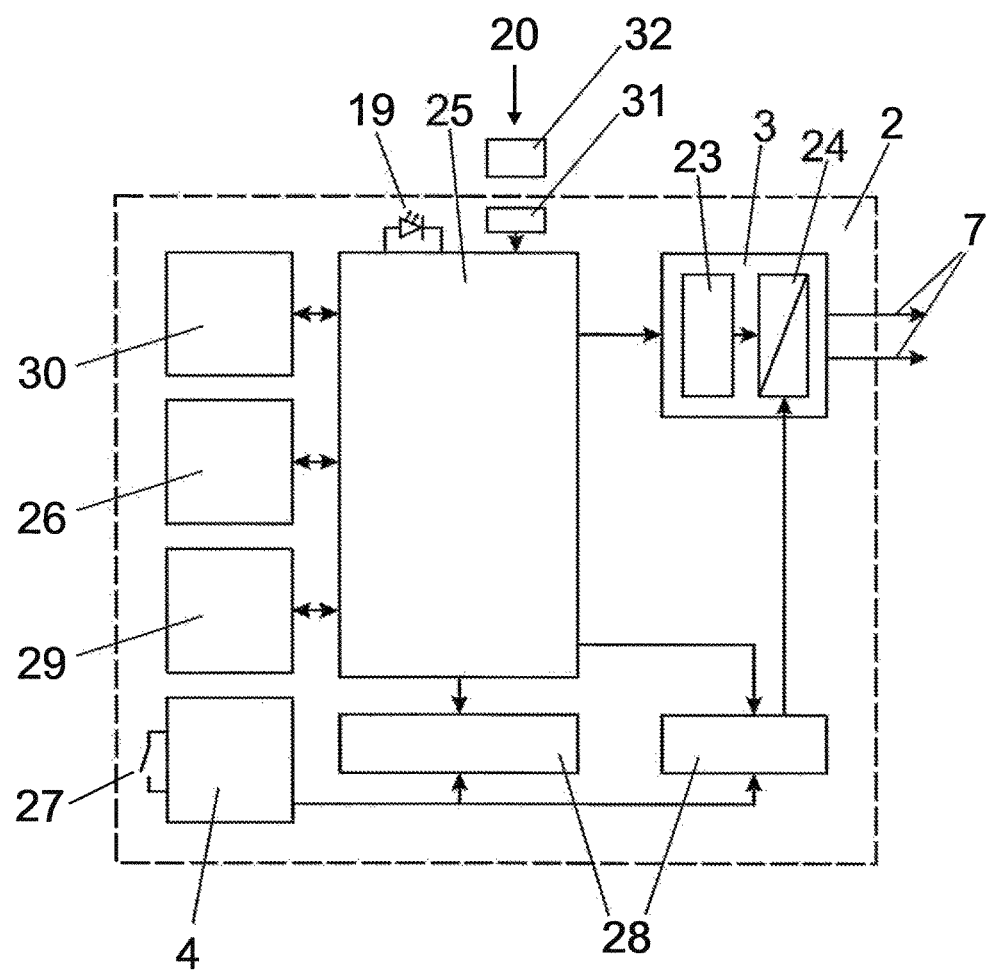
FIG. 6 shows a block diagram of an embodiment of the stimulator.

FIG. 6 shows a block diagram of an embodiment of a stimulator 2 of the electrical stimulation device 1. Here, the generator 3 for generating electrical stimulation pulses is formed by a digital-to-analogue converter 23 and a voltage-to-current converter 24. The needle electrodes 5 (not illustrated) are connected to the stimulator 2 via the lines 7. The voltage supply 4 is preferably formed by a battery. A control device 25 is provided for controlling the generator 3 and specifying the stimulation parameters and controlling the stimulation process. The generator 3 of the stimulator 2 is preferably designed for generating stimulation pulses having a repetition rate of 0.5 to 100 Hz, preferably 1 Hz, and a duty cycle of 10 to 90%, preferably 50%. Such stimulation parameters have proven preferable in applications in pain therapy or the healing of wounds. Since the impedance of the skin is subject to large variations, it is advantageous if the stimulation pulses are generated having a constant current amplitude. The control device 25 is preferably formed by a suitable microcontroller. The control device 25 may be programmed and/or its parameters may be changed via an interface 26. Changing the stimulation parameters may also be performed manually from the outside via suitable control elements 20 that are connected to the control device 25. For example, the control elements 20 may be formed by a suitable Hall sensor 31 which is connected to the control device 25 and may be actuated via a magnet 32. The current amplitude of the stimulation pulses, for example, may be set and changed via the control element 20. A switch 27 may be used for activating the stimulator 2 and/or the voltage supply 4 provided therein. Advantageously, however, such a switch 27 is omitted and the activation of the stimulator 2 occurs automatically when plugging the needle electrodes 5 into the stimulator 2. In order to obtain that stimulation pulses having a consistent current amplitude may be output by the needle electrodes 5, appropriate regulators 28 are connected to the control device 25, which are in turn connected to the voltage-to-current converter 24.

Furthermore, a timer 29 may be connected to the control device 25, specifying the duration of stimulation and the pattern of stimulation. If the stimulator 2 has a memory 30, the stimulation parameters may be recorded, depending on the time, for later examinations or for quality control. The memory 30 may be read by a suitable computer via the interface 26.

For indicating proper operation of the stimulation device 1 and/or the stimulator 2, a corresponding operation indicator 19 may be provided, which may be implemented by a light-emitting diode, for example.

Figure 7:
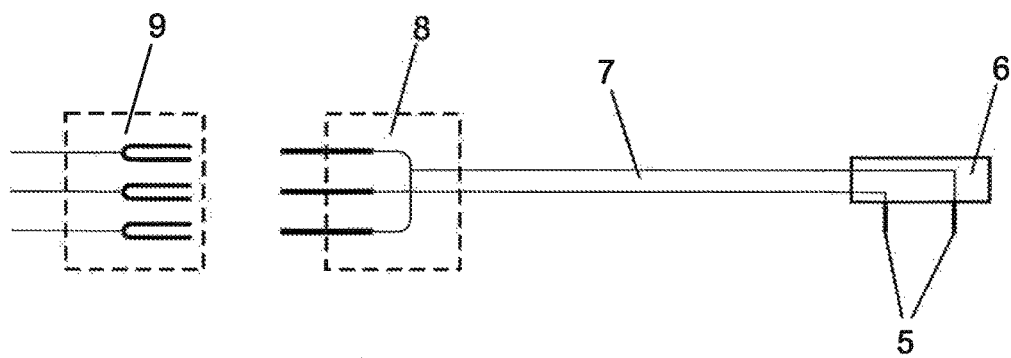
FIG. 7 shows the circuit of the plug on the line of the needle electrodes.

FIG. 7 shows the principle of the circuit of the plug 8 on the line 7 of the needle electrodes 5, which has already been mentioned briefly above with reference to FIGS. 2 and 3. According to this, the plug 8 has three contacts the outer two of which are connected to one needle electrode 5 and the middle one is connected to the other needle electrode 5. In this way, an automatic activating of the stimulator 2 may be obtained together with a corresponding circuit (not illustrated) of the jack 9 when connecting the plug 8 to the jack 9 since the outer contacts of the plug 8 allow connecting and/or switching.

Figure 8:
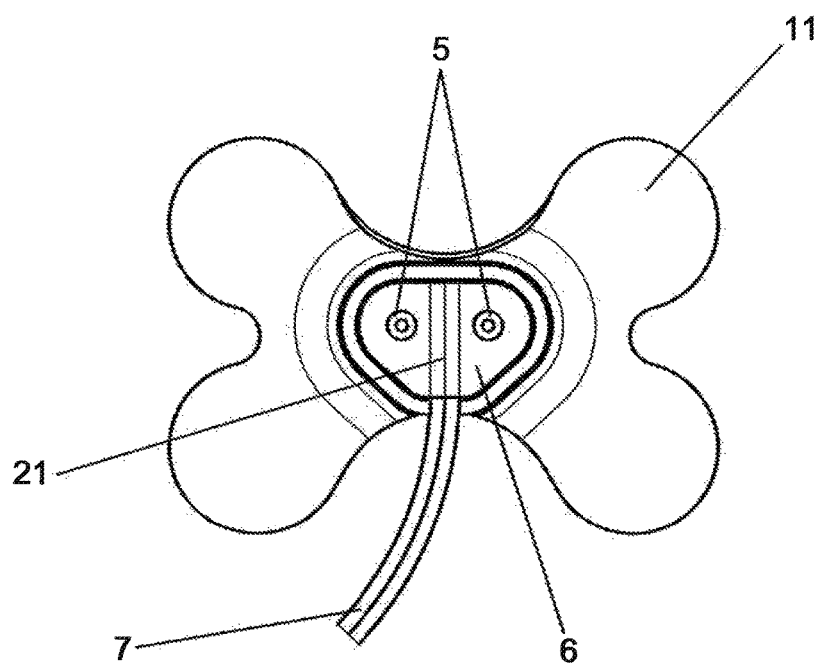
FIG. 8 shows a bottom view of an embodiment of the electrode housing.

Finally, FIG. 8 shows a bottom view of an embodiment of an electrode housing 6 having two needle electrodes 5. Between the needle electrodes 5, a notch 21 is disposed, which avoids a short circuit between the needle electrodes 5, for example because of sweat, and/or prevents the production thereof and thus prevents malfunctions of the stimulation device 1. By means of an appropriately designed adhesive foil 11, the electrode housing 6 may be attached to the surface of the skin of the patient in the area to be stimulated. The adhesive foil 11 has suitably projecting tabs in order to increase the adhesive area and obtain a secure attachment to the corresponding area of the surface of the skin to be stimulated. Depending on which region of the body is to be stimulated, the adhesive foil 11 may be designed differently in an appropriate way.

The invention claimed is:

1. An electrical stimulation device (1) having a stimulator (2), containing a generator (3) for generating electrical stimulation pulses having specific stimulation parameters, a voltage supply (4) for supplying the generator (3) with electrical energy and a stimulator housing (13), and having at least two needle electrodes (5) for piercing the surface of the skin of an area to be stimulated, which needle electrodes (5) are connected to the stimulator (2) via a line (7), wherein the stimulator (2) can be releasably connected to a fastening element (14) for fastening the stimulator (2) to the surface of the skin, characterized in that the fastening element (14) has a clip (15) with arms for releasably receiving the stimulator housing (13) and a support element (16) for supporting and fastening the stimulator (2) to the surface of the skin, wherein the clip (15) is oriented at substantially 90° to the support element (16), wherein the clip (15) of the fastening element (14) has latching elements (17) for snapping into at least one groove (18) in the stimulator housing (13) or wherein the stimulator housing (13) has latching elements (17) for snapping into at least one groove in the clip (15) of the fastening element (14) and wherein a lever 22 for spreading the arms of the clip (15) of the fastening element (14) and lifting the latch elements (17) out of the groove (18) is disposed on the clip (15) of the fastening element (14).

2. The electrical stimulation device (1) according to claim 1, characterized in that the clip (15) has latching elements (17) for snapping into at least one groove (18) in the stimulator housing (13).

3. The electrical stimulation device (1) according to claim 2, characterized in that the at least one groove (18) is disposed asymmetrically on the stimulator housing (13) so the stimulator housing (13) may only be connected to the fastening element (14) in one orientation.

4. The electrical stimulation device (1) according to claim 1, characterized in that the at least two needle electrodes (5) are disposed in a common electrode housing (6).

5. The electrical stimulation device (1) according to claim 4, characterized in that an adhesive foil (11) is provided for attaching the electrode housing (6) to the surface of the skin.

6. The electrical stimulation device (1) according to claim 4, characterized in that a notch (21) is disposed between the at least two needle electrodes (5) on the side of the electrode housing (6) facing the surface of the skin.

7. The electrical stimulation device (1) according to claim 1, characterized in that an adhesive foil (12) is provided for attaching the fastening element (14) to the surface of the skin.

8. The electrical stimulation device (1) according to claim 7, characterized in that the adhesive foil (12) has a much larger contact area than the fastening element (14) and projects over it.

9. The electrical stimulation device (1) according to claim 1, characterized in that the line (7) is provided with at least one plug (8) for releasably connecting it to a corresponding jack (9) in the stimulator (2) or the electrode housing (6).

10. The electrical stimulation device (1) according to claim 9, characterized in that the at least one plug (8) is designed waterproof.

11. The electrical stimulation device (1) according to claim 1, characterized in that an operation indicator (19) is provided on the stimulator (2).

12. The electrical stimulation device (1) according to claim 1, characterized in that a control element (20) is provided on the stimulator (2).

13. The electrical stimulation device (1) according to claim 12, characterized in that the control element (20) is formed by a Hall sensor (31) that may be actuated by a magnet (32).

14. The electrical stimulation device (1) according to claim 1, characterized in that the stimulator (2) has a timer (29) for automatically specifying the duration of stimulation.

* * * * *